United States Patent [19]
Kleinman

[11] 4,403,337
[45] Sep. 6, 1983

[54] AUTOMATED SETTING OF TECHNIC FACTORS FOR X-RAY EXAMINATIONS
[75] Inventor: Bennett Kleinman, Amityville, N.Y.
[73] Assignee: Bennett X-Ray Corp., Copiague, N.Y.
[21] Appl. No.: 321,522
[22] Filed: Nov. 16, 1981
[51] Int. Cl.³ .............................................. G03B 41/16
[52] U.S. Cl. ................................................. 378/95; 378/96
[58] Field of Search ..................................... 378/95, 96
[56] References Cited

U.S. PATENT DOCUMENTS 3,448,606  6/1969  Flaherty ................................. 378/99
3,997,793 12/1976  Rogers ................................. 378/205
4,039,836  8/1977  Shaw ................................... 378/95

Primary Examiner—Craig E. Church

[57] ABSTRACT

Disclosed is automated setting of x-ray technic factors (KV, MA and exposure time) on the basis of (a) automated determination of the thickness of the patient part to be imaged by a non-contact, sonic ranging system, (b) push button selection for the type of examination, and (c) push button selection for the type of patient physique. The automatically determined technic factors and/or thickness are displayed to allow for manual override, and other failsafe features are provided as well.

3 Claims, 1 Drawing Figure

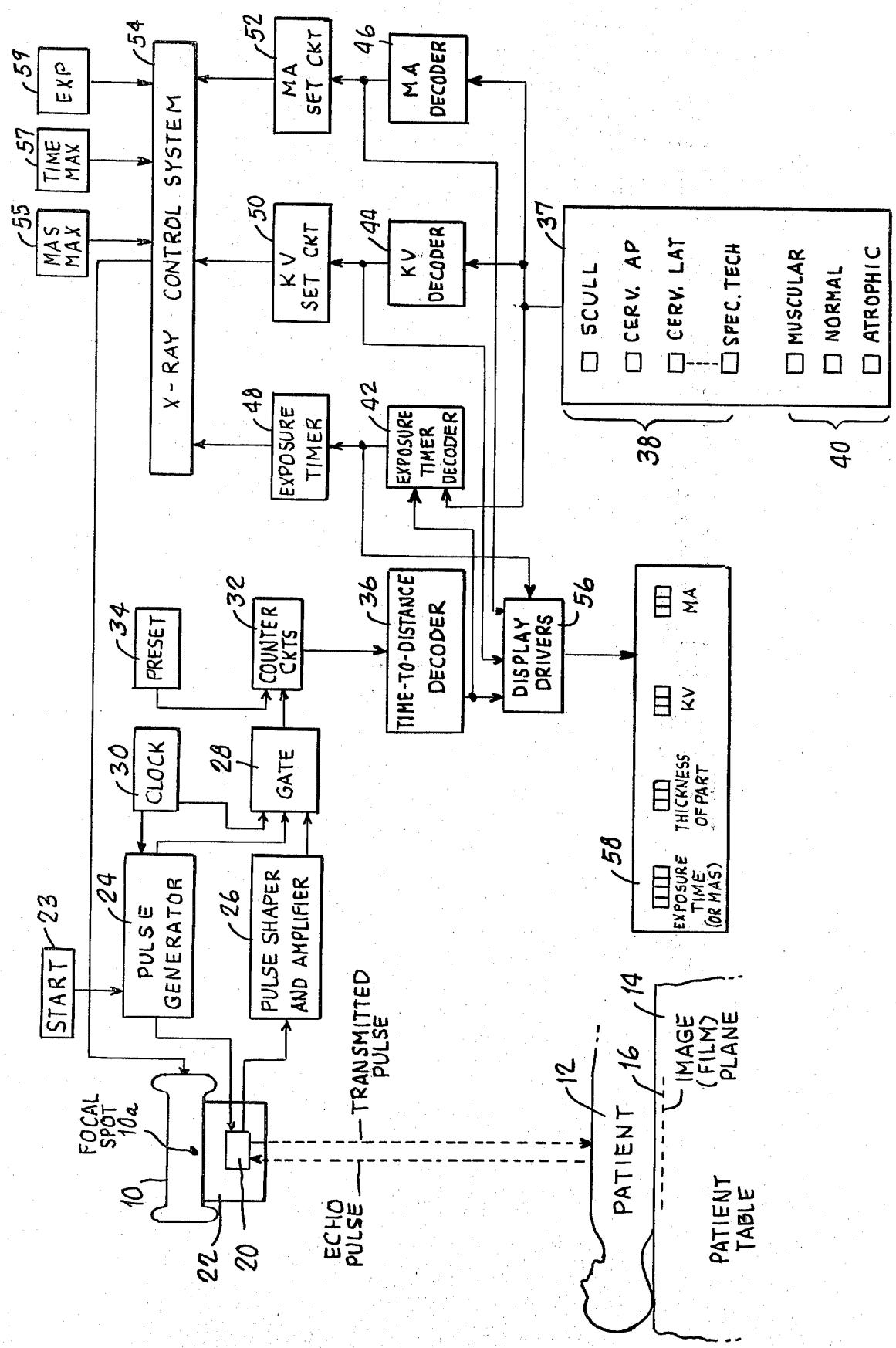

AUTOMATED SETTING OF TECHNIC FACTORS FOR X-RAY EXAMINATIONS

BACKGROUND AND SUMMARY OF THE INVENTION

The invention relates to medical x-ray machines and specifically to automated setting of technic factors such as exposure time, KV (the operating voltage to be applied to the x-ray tube) and MA (the current in milliamperes to be supplied to the x-ray tube).

In medical x-ray machines it is important to select technic factors which avoid exposing the patient to any unneeded radiation and yet produce a picture which is clear enough to be useful for diagnostic purposes. Normally three factors are set for a particular examination: the voltage and current (in KV and MA) which will energize the x-ray tube and the exposure time. The criteria for determining an optimum combination of KV, MA and exposure time include the distance between the focal spot from which x-rays emanate and the image plane (e.g., the x-ray film plane), the type of examination or procedure (e.g., an examination of the pelvis, the skull, the stomach, the esophagus, etc.) and the thickness of the patient part which is to be imaged. Standard technic charts are published and used in the industry to find the KV, MA and exposure time for the given type of examination and for a given thickness of the body part to be imaged. In a typical prior art examination the patient is positioned against the image receptor or patient support, the x-ray technician measures the thickness of the body part to be imaged, using calipers or some other mechanical instrument, looks up the corresponding technic factors on the chart, and sets corresponding KV, MA and exposure time (or only KV and MAS—milliamperes per second) controls on a panel. The procedure is time consuming and, of course, prone to human error in that the technician may incorrectly look up or set the necessary technic factors and the patient may meanwhile move and thereby change the thickness of the part which is actually imaged.

In one known prior art system an ionization chamber is positioned adjacent the image plane to detect when the image receptor has received sufficient radiation for a clear image and to then de-energize the x-ray tube. However, the system is so expensive and requires so much careful calibration that it is believed to be rarely used outside large and sophisticated radiology centers, and it is believed that most users still rely on manually measuring the thickness of the body part to be imaged and manually setting the technic factor controls.

In view of the known prior proposals, an object of the invention is to provide a system in which a non-contact, automatic sonic measurement is made of the thickness of the patient part to be imaged and this measurement is automatically used together with technician-selected type of examination and type of patient information for automatic setting of an optimum combination of technic factors. Another object of the invention is to provide such a system which is relatively inexpensive to make and reliable and convenient to use. Other objects will become apparent from the detailed description below of an exemplary, nonlimiting example of the invention.

In an exemplary embodiment, an x-ray machine includes an x-ray source and an image receptor, such as film in a suitable holder, which has an image plane at a known (or determinable) distance from the source and is illuminated with x-rays therefrom when the source is energized. The patient is positioned against a patient support, on a patient table or against an upright support, such that the distance between the image plane and the patient part to be imaged is fixed but the distance between the part and the source is unknown—as it is determined by the unknown thickness of the part to be imaged. A sonic transducer fixed with respect to the source sends a sonic signal toward the patient part to be imaged and receives its sonic reflection therefrom. A travel time derivation circuit is coupled with the sonic transducer and derives therefrom a signal determined by the two-way travel time of the sonic signal, i.e., the time the sonic signal takes to travel from the transducer to the patient and back from the patient to the transducer. The two-way travel time signal is converted to a thickness signal defining the thickness of the patient part to be imaged, and an exposure time derivation circuit derives, in part on the basis of that thickness signal and in part on the basis of technician-selected push buttons for the type of x-ray examination and for the type of patient physique, a signal defining the exposure time for imaging said patient part. The type-of-examination and type-of-patient-physique push buttons (or other manually operated devices) which are manually set by the technician automatically determine the KV and MA at which the x-ray source will be operated. The system periodically rechecks the patient thickness and, if necessary, updates the automatic exposure time selection, until the technician pushes a button (or operates some other control) to initiate actual x-ray exposure at the so selected technic factors. Failsafe provisions are made against exceeding a maximum permissible exposure time which can be selected by the technician for the particular type of examination and/or patient, and maximum permissible MAS (current flow per second to the x-ray tube).

BRIEF DESCRIPTION OF THE DRAWING

The FIGURE is a partly schematic and partly functional block diagram illustrating an exemplary embodiment of the invention.

DETAILED DESCRIPTION OF AN EXEMPLARY EMBODIMENT

An x-ray tube 10 when energized generates at its focal spot 10a x-rays which illuminate a patient 12 positioned on a patient table 14. The x-rays which pass through patient 12 illuminate an image receptor 15, such as a film holder which has an image (film) plane at 16. For a given examination, the distance between focal spot 10a and image plane 16 is fixed and known (or can be determined). For example, in radiographic examinations the distance is typically either 40 inches or 72 inches. What is not initially known, because it depends on the shape, size and position of the patient part to be imaged, is the thickness of patient tissue through which x-rays must pass in order to reach image receptor 15. Knowing this thickness is important because it must be taken into account in determining the optimum technic factors. The relevant thickness is measured herein with the help of a sonic transducer 20 mounted at the outside of a collimator box 22 which in turn is mounted on x-ray tube 10. When energized by pulse generator 24, transducer 20 sends a transmitted pulse toward patient 12, and the facing surface of the patient's body reflects it as an echo pulse. Upon receipt of the echo pulse transducer 12 generates an electrical signal supplied to a pulse shaper and amplifier 26 which is a part of a travel time circuit 27 also including a gate 28, clock 30, counter circuit 32 and pre-set circuit 34. Clock 30 runs at a high frequency relative to the typical two-way travel times of the sonic signal from transducer 20, e.g., at 550 KHz. Gate 28 opens under the control of a signal from pulse generator 24 at the time transducer 20 sends out the transmitted pulse and closes under the control of a signal from pulse shaper and amplifier 26 at the time transducer 20 receives the reflected echo pulse. Accordingly, gate 28 supplies to counter 32 those pulses from clock 30 which occur during the time interval over which the transmitted pulse travels from transducer 20 to patient 12 and the echo thereof travels from patient 12 back to transducer 20. Pre-set circuit 34 loads a first portion of counter circuit 32 with a count which corresponds to the two-way travel time between transducer 20 and the surface of patient table 14, and the pulses supplied to counter circuit 32 from gate 28 are counted up in a second portion of counter circuit 32. The counts in the first and second portions of counter circuit 32 are subtracted therein from each other and the difference signal, which is determined by and thereby defines the thickness of the patient part to be imaged by image receptor 15, is supplied to a time-distance decoder 36 which converts it to a thickness signal defining the thickness, e.g. in centimeters, of the patient part to be imaged, i.e. that part of patient 12 which is between x-ray source 10 and transducer 20 on the one hand and image receptor 15 on the other.

The thickness signal from decoder 36 is supplied to an exposure time decoder 42 which receives an additional input from a control panel 37 having a set of push buttons 38 for selecting the type of examination or procedure to which patient 12 is to be subjected and a set of push buttons 40 for indicating the type of patient physique. The purpose of decoder 42 is to convert the measurement of patient part thickness supplied from decoder 36 and the selections made on control panel 37 into a signal defining the exposure time for the x-ray examination to follow.

The signals from control panel 37 are also supplied to a KV decoder 44 and an MA decoder 46. Decoder 44 provides a signal which defines a particular KV level depending on which button or buttons on control panel 37 are pushed in, and decoder 46 similarly supplies a signal which defines a particular MA level depending on which button or buttons are pushed on control panel 37. The outputs of decoders 42, 44 and 46 are supplied, respectively, to exposure timer 48, KV set circuit 50 and MA set circuit 52, which in turn supply their outputs to x-ray control system 54. Control system 54 controls the supply of power to x-ray tube 10 and, under the control of a technician-operated switch 59, energizes x-ray tube 10 during an exposure time window determined by timer 48 and at a KV level determined by KV set circuit 50 and with current determined by MA set circuit 52. Failsafe controls are provided in that regardless of its input from timer 48 and circuit 52, control system 54 never operates x-ray tube at a level exceeding a maximum permissible MAS (milliamperes per second), set at a circuit 55, e.g. 600 MAS, and never exceeds a maximum permissible exposure time set manually by the technician at circuit 57 for a given type examination and/or for a given patient physique.

In operation, pre-set circuit 34 is manually set to a fixed SID (focal spot to image plane distance), e.g. 40 inches or 72 inches, and is left at that setting for as long as the corresponding relationship between x-ray tube 10 and patient table 14 is left undisturbed. A particular type of examination is selected by pushing in one of buttons 38, and the type of patient physique is accounted for by pushing in one of buttons 40 on control panel 37. The resulting output of control panel 37 is decoded by decoders 44 and 46 and sets the KV level at circuit 50 and the MA level at circuit 52. The outputs of decoders 44 and 46 are additionally supplied to display drivers 56 to energize a 3-digit or meter KV display and a 3-digit MA display in unit 58 showing the resulting KV and MA selections. The patient is then positioned on table 14 (or against a corresponding upright support in case of a stand-up examination), with the part to be imaged immediately above (or adjacent) image receptor 15, and a start switch 23 is energized to turn on pulse generator 24 and to thereby cause transducer 20 to send out a transmitted pulse whose echo is processed as discussed above to produce a distance signal at the output of decoder 36. This thickness signal is supplied to display drivers 56 and is displayed, in centimeters, at the correspondingly labelled display in unit 58, and is additionally supplied to exposure time decoder 42 to help set exposure timer 48 as discussed above. When the technician is satisfied with the position of the patient and, as a precaution, with the exposure time (or MAS), thickness, KV and MA displayed at unit 58, an exposure switch 59 is manually energized to cause x-ray control system 54 to energize x-ray tube 10 over the exposure time interval determined by timer 48 and at the KV and MA determined by circuits 50 and 52 respectively. Switch 59 is interlocked with exposure timer 48 (through a circuit not shown in the drawing) such that the energization of switch 59 has no effect on x-ray control system 54 until after the setting of timer 48 by an output from decoder 42 has been completed. In addition, failsafe circuits 55 and 57 constrain x-ray control system 54 such that the energization of switch 59 has no effect on x-ray tube 10 if the relationship between the contents of timer 48 and MA circuit 52 are such that the MAS indicated thereby exceeds the maximum MAS set in circuit 55 or if the exposure time set in timer 48 exceeds a maximum exposure time set in circuit 57 by the technician for the given type of examination and/or patient physique.

Once a patient has been positioned on or against patient support 14, the system keeps rechecking the relevant thickness measurement until an x-ray exposure is actually taken. To that end, pulse generator 24 receives an input from clock 30 which enables it to energize transducer 20 a fixed number of times per second, for a corresponding number of updates of thickness measurements. The clock pulses from gate 28 for each new thickness measurements replace the clock pulses previously accumulated in the second part of counter circuits 32 for a previous thickness measurement, and the new thickness measurement updates the thickness display at unit 58 and the contents of exposure timer 48. As noted earlier if exposure switch 59 is energized while the contents of exposure timer 48 are being updated, x-ray control system 54 waits until the updating of exposure timer 48 is completed before energizing x-ray source 10 on the basis of the contents of exposure timer 48, KV set circuit 50 and MA set circuit 52. Once x-ray control system 54 commences the energization of x-ray source 10, further changes in the contents of timer 48 and circuits 50 and 52 have no effect on x-ray control system 54 until the x-ray exposure is completed.

In an exemplary implementation, each of decoders 44 and 46 can comprise an EPROM device storing three look-up tables. In a given decoder, each table is for a respective one of the three push buttons 40, and each table stores a respective digital signal for each respective one of push buttons 38. For a given one of decoders 44 and 46 the relationship between the three tables is such that for a given one of the push buttons 38 the signal level for the push button 40 labelled MUSCULAR is 1.4 times that of the signal for the push button 40 labelled NORMAL and the signal stored for the push button 40 labelled ATROPHIC is 0.6 times that stored for the push button labelled NORMAL. For example, referring to MA decoder 46, in the case of the look-up table for the push button 40 labelled NORMAL a signal indicative of 300 milliamperes is stored for the push button 38 labelled SKULL, and a signal indicative of 100 milliamperes is stored for the push button 38 labelled LUMBAR SPINE. In the case of the push button 40 labelled MUSCULAR the corresponding signal for SKULL is 420 milliamperes and for the push button labelled ATROPHIC the same signal is 180 milliamperes. Decoder 42 can similarly comprise an EPROM circuit containing a respective look-up table for each respective one of push buttons 38 and a respective multiplier for each of push buttons 40. Each table stores a respective exposure time value for each of several thickness signals within the range of thickness expected for the respective push button switch 38. The multiplier for the push button 40 labelled MUSCULAR multiplies the exposure time signal derived from the look-up tables for a given thickness and a given push button 38 by 1.4 prior to supplying it to exposure timer 48; the multiplier for push button 40 does the same multiplication by a factor of 1.0; and the multiplier for the push button 40 does the same multiplication by a factor of 0.6. For example, the look-up table for the push button 38 labelled SKULL contains a signal indicative of an exposure time of 1/12th of a second when the thickness signal from decoder 36 indicates 18 centimeters, and contains additional exposure time signals for other thickness signals increasing the exposure time by increments corresponding to 5 MAS per centimeter increase in the thickness dimension. In the case of a chest x-ray selected by a correspondingly labelled push button 38, the respective look-up table in decoder 42 stores an exposure time signal for 1/30th of a second for a chest thickness dimension of 22 centimeters, the exposure time signal increasing by increments corresponding to 1.25 MAS for each centimeter increase in the thickness dimension provided by decoder 36. Of course, the particular values indicated above correspond to a particular selection, and for any given application other relationships between thickness, type of examination, type of patient physique, MA and KV can be selected and appropriately stored in the look-up tables and multipliers discussed above. Pulse generator 24 can be energized, to initiate a new thickness measurement 3 times per second, but of course this is an arbitrary selection, and a different frequency of rechecking can be selected. The output of decoder 42 can be supplied to display drivers 56 and displayed at the correspondingly labelled 4-digit display at unit 58 or, as an alternative, the product of the outputs of decoders 46 and 42, which is the MAS factor for the examination, can be supplied to display drivers 56 and displayed in place of the exposure time in unit 58. The transmitted sonic pulse from transducer 20 can be a combination of several cycles at several different frequencies: for example, each transmitted pulse can comprise eight cycles at 60 KHz, eight cycles at 57 KHz, sixteen cycles at 53 KHz and twenty-four cycles at 50 KHz.

As one example the system discussed above for automatically setting technic factors can be incorporated in an x-ray machine of the type available from the Bennett X-Ray Corp. under the designations RD 325, 525 and 625, and it should be clear that for the sake of conciseness the discussion above omits an express description of conventional and well known parts of such an x-ray machine, such as a power supply for the x-ray tube, appropriate mechanical supports for the x-ray source and the patient table, etc., and for the same reason omits an express description of the conventional aspects of the circuitry shown in the drawing and discussed above, such as power supplies, detailed relative timing, etc. It should also be clear that the discussion above relates to a particular exemplary embodiment of the invention but is not limited thereto and includes other embodiments and implementations thereof, such as in a fluoroscopic or other type of x-ray machine, and that the scope of the invention is defined only in the appended claims.

I claim:

1. A medical x-ray machine comprising:

an x-ray source and an image receptor having an image plane which is at a known distance from the source and is illuminated with x-rays therefrom when the source is energized;

a patient support for locating a patient between the source and image plane such that the distance between the image plane and the patient part to be imaged is fixed but the distance between the part and the source is determined by the unknown thickness of said part;

a sonic transducer which is fixed with respect to the source and sends a sonic signal toward the patient part to be imaged and receives its sonic reflection therefrom;

a travel time derivation circuit coupled with the sonic transducer for deriving therefrom a signal determined by the two-way travel time of the sonic signal between the transducer and the patient part to be imaged;

means for converting the two-way travel time signal to a thickness signal defining the thickness of the patient part to be imaged;

an exposure time circuit responsive to said thickness signal for deriving, at least in part on the basis thereof, a signal defining an exposure time for imaging said patient part; and means for energizing the x-ray source over an exposure time interval determined at least in part on the basis of said exposure time signal.

2. A medical x-ray machine comprising:

an x-ray source and an image receptor illuminated with x-rays therefrom when the source is energized;

means for locating a patient at a fixed distance from the image receptor;

a sonic transducer which is at a known distance from the receptor and sends a sonic signal toward the patient from the direction of the source and receives the sonic reflection of said signal from the side of the patient facing the source;

means for timing the travel time of said sonic signal to derive therefrom a thickness signal related to the thickness of the patient part to be imaged; and means utilizing said thickness signal in automatically setting the exposure time for an x-ray examination of said patient part.

3. A medical x-ray examination method comprising:
positioning a patient against an image receptor, with the patient part to be imaged facing an x-ray source, and utilizing a sonic transducer which is at a known distance from the image receptor to send a sonic signal from the direction of the source and to receive the reflection thereof from the patient part facing the source; and automatically setting the x-ray exposure time at least in part on the basis of the travel time of said sonic signal.

* * * * *